United States Patent
Curiel et al.

(10) Patent No.: US 6,649,396 B1
(45) Date of Patent: Nov. 18, 2003

(54) FIBER RECEPTOR-INDEPENDENT SYSTEM FOR THE PROPAGATION OF ADENOVIRAL VECTORS

(75) Inventors: David T. Curiel, Birmingham, AL (US); Igor Dmitriev, Homewood, AL (US); Victor N. Krasnykh, Birmingham, AL (US); Joanne T. Douglas, Huntsville, AL (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/498,134

(22) Filed: Feb. 3, 2000

Related U.S. Application Data

(60) Provisional application No. 60/118,880, filed on Feb. 5, 1999.

(51) Int. Cl.[7] .............................. C12N 7/01; C12N 5/06; C12N 5/16; C12N 15/09; C12N 15/85; C12N 15/86

(52) U.S. Cl. ................... 435/235.1; 435/69.3; 435/455; 435/326

(58) Field of Search ................................. 435/7.2, 69.1, 435/69.3, 235.1, 173.1, 325, 326, 320.1, 334, 361, 362, 455, 456; 436/501; 530/328, 379

(56) References Cited

U.S. PATENT DOCUMENTS 6,210,946 B1 * 4/2001 Curiel et al. ............. 435/235.1

FOREIGN PATENT DOCUMENTS

WO     WO 98//54346    * 12/1998

OTHER PUBLICATIONS

Dmitriev et al. Journal of Virology. 1998; 72 (12): 9706–9713.*
Ridder et al. 1995. A COS cell–based system for rapid production and quantification of scFv::lgCk antibody fragments. vol. 166. No. 2, pp. 273–276.*
Irusta et al. 1998. A single amino acid substitution in a WW–like domain of diverse members of the PDGF receptor subfamily of tyrosine kinases causes constitutive receptor activation. Vol 17. No. 23, pp. 6912–6923.*

* cited by examiner

Primary Examiner—James Housel
Assistant Examiner—Shanon Foley
(74) Attorney, Agent, or Firm—Benjamin Aaron Adler

(57) ABSTRACT

The present invention provides a means for the propagation of adenovirus lacking the native tropism by using genetic methods to modify the fiber protein by addition of a C-terminal tag. The modified virus is then propagated in a cell line transfected with a sequence encoding an artificial receptor for the C-terminal tag on the modified fiber protein.

1 Claim, 10 Drawing Sheets

FIBER RECEPTOR-INDEPENDENT SYSTEM FOR THE PROPAGATION OF ADENOVIRAL VECTORS

CROSS-REFERENCE TO RELATED APPLICATIONS

This application claims benefit of provisional application U.S. Ser. No. 60/118,880, filed Feb. 5, 1999, now abandoned.

FEDERAL FUNDING LEGEND

This invention was created in part using funds from the National Institutes of Health under grants CA 74242 and HL 50255. The federal government, therefore, has certain rights in this invention.

BACKGROUND OF THE INVENTION

1. Field of the Invention

The present invention relates generally to the fields of virology and gene therapy. More specifically, the present invention relates to the production of recombinant adenoviral vectors with modified fibers for the purpose of cell-specific targeting with the additional advantage of concomitant elimination of endogenous tropism.

2. Description of the Related Art

Recombinant adenovirus vectors are used in a number of gene therapy applications principally because of the high levels of gene transfer achievable with this approach both in vitro and in vivo. In addition, recombinant adenovirus vectors are distinguished from other available systems by their unique ability to accomplish in situ gene delivery to differentiated target cells in a variety of organ contexts.

Recombinant human adenovirus vectors of serotypes 2 (Ad2) and 5 (Ad5) have the ability to transfer genes to a range of cell types in vivo efficiently and have therefore been employed in a number of gene therapy approaches. However, it is not currently possible to exploit the full potential of adenovirus as a gene delivery vehicle exhibiting systemic stability following intravenous administration. Adenovirus-mediated delivery of a therapeutic gene selectively to target disease cells is precluded by the widespread distribution of primary cellular receptors for Ad2 and Ad5. In addition, it has recently been reported that a number of tissues which represent important targets for gene therapy, including the airway epithelium and primary tumors, express only low levels of primary adenovirus receptors and are thus poorly transduced by adenovirus vectors (1–4). Therefore, strategies are being developed to alter the tropism of the adenovirus vector to permit efficiently targeted gene delivery to specific cell types.

Two distinct, sequential steps are required for the entry of adenoviruses into susceptible cells. In the first step, Ad2 and Ad5 bind with high affinity to the primary cellular receptors, identified as the coxsackievirus and adenovirus receptor CAR (5–7), and the α2 domain of the major histocompatibility complex (MHC) class I protein (8). This binding occurs via the C-terminal knob domain of the adenovirus fiber protein (9,10). The second subsequent step is the internalization of the virion by receptor-mediated endocytosis potentiated by the interaction of Arg-Gly-Asp (RGD) peptide sequences in the penton base with secondary host cell receptors, integrins $\alpha_v\beta_3$ and $\alpha_v\beta_5$ (11,12). The virion then escapes from the endosome and localizes to the nuclear pore whereupon its genome is translocated to the nucleus.

Strategies to alter adenovirus tropism are based on modifications of the viral capsid proteins to permit the recognition of alternative cell-specific receptors. Modification of adenovirus tropism by complexing adenovirus particles with bispecific conjugates that simultaneously ablate endogenous viral tropism and introduce novel tropism has been the main approach to date (4, 13–21). This approach to the generation of targeted adenovirus vectors suffers from a number of limitations that could be avoided by the direct genetic engineering of the viral capsid proteins to contain cell-targeting ligands. In this regard, the C-terminus of the adenovirus fiber protein can be modified to incorporate targeting motifs with specificity for cellular receptors (22–24).

In an alternative approach, targeting ligands can be incorporated within the so-called HI loop of the fiber knob (3, 25). These genetic modifications to the fiber protein have resulted in expanded tropism by redirecting adenovirus binding to alternative cellular receptors. However, these modified vectors also retain the ability to recognize the fiber receptor; native tropism has not been abolished.

Thus, to date, it has not, proven possible to employ genetic methods to engineer adenovirus vectors with specificity for a single target cell type. In addition to recognizing novel receptors, such vectors should also lack the ability to bind to the native primary adenovirus receptor. This can be accomplished either by site-directed mutagenesis of the fiber knob domain to eliminate the cell-binding site or by complete replacement of the fiber knob. However, an important consequence of the ablation of native adenovirus tropism is that it is not possible to propagate these vectors in standard, packaging cell lines that express the fiber receptor such as 293 (26) and 911 (27). Hence, it is necessary to construct alternative cell lines expressing novel primary receptors that can b e recognized by adenovirus vectors that fail to bind the fiber receptor.

The prior art is deficient in the lack of a fiber receptor-independent system for the propagation of adenoviral vectors and genetically modified adenovirus vectors with specificity for a single target cell type. The present invention fulfills this longstanding need and desire in the art.

SUMMARY OF THE INVENTION

Genetic modifications to the knob domain of the fiber protein of vectors based on human adenovirus serotype 5 (Ad5) have resulted in expanded tropism by redirecting adenovirus binding to alternative cellular receptors. However, native tropism has not been abolished to date: the vectors retain the ability to recognize the fiber receptor. An important consequence of strategies to ablate native adenovirus tropism is that it is not possible to propagate these modified vectors on standard cell lines that express the fiber receptor. Hence, it is necessary to construct alternative cell lines expressing novel primary receptors that can be recognized by adenovirus vectors that fail to bind the fiber receptor.

Towards this goal, two distinct artificial primary cellular receptors for Ad5 were generated. The extracellular domain of one of the synthetic receptors was derived from a single-chain antibody (sFv) with specificity for Ad5 knob, while the second receptor consisted of an icosapeptide identified from a phage display library by biopanning against Ad5 knob. Expression of either of these artificial receptors in fiber receptor-negative cells conferred susceptibility to Ad5 infection. Having shown the feasibility of engineering novel primary receptors for Ad5, an Ad5 vector was then genetically modified by incorporating six histidine (His) residues at the C-terminal of the fiber to serve as a motif specifically to mediate propagation of the vector. This vector could be amplified in fiber receptor-negative cells engineered to express an artificial surface receptor comprising an anti-His tag sFv. This novel fiber receptor-independent system for the propagation of adenovirus viruses is being used for the generation of vectors lacking native tropism.

In the present invention, there is provided a composition of matter comprising a method of propagating adenovirus independent of the ubiquitous adenovirus fiber protein receptor. An artificial, recombinant receptor is expressed in a host cell line which interacts with a surface protein on the virion other than the fiber protein gene. This enables the fiber protein receptor binding domain of the fiber protein to be altered to eliminate native tropism of the virus while still allowing the modified virus to be propagated in the host cell line.

In another embodiment of the current invention, the artificial receptor is specific for a recombinant protein marker expressed on the surface of the adenovirus.

In yet another embodiment of the current invention, the novel protein marker on the adenovirus surface is a recombinant protein tag added to the C-terminal end of the adenovirus fiber protein. This is recognized an artificial receptor containing an sFv specific for the said novel protein tag. In a preferred embodiment, the novel protein tag contains six C-terminal histidine and is recognized by an sFv from an anti-His tag monoclonal antibody.

The current invention includes the recombinant, artificial receptor designed to allow adenovirus propagation. This receptor comprises a signal peptide to direct the receptor to the cellular secretory pathway; a transmembrane domain for anchoring the receptor in the plasma membrane; and a protein binding domain specific for the protein marker with which the receptor is to associate. In the representative examples given herein, the artificial receptor is constructed with a signal peptide from the Ig-K leader sequence, and a transmembrane domain from the Platelet Derived Growth Factor Receptor (PDGFR). It also includes HA and Myc epitopes for immunological detection of the receptor. In the preferred embodiment described herein, the artificial contains an sFv derived from an anti-His tag monoclonal antibody.

The current invention also includes a recombinant adenovirus expressing an novel protein marker which can b e recognized by a specific artificial receptor. The adenovirus may also contain other genes such as therapeutic genes, transgenes for genomic modification, and marker genes for adenovirus detection.

In another embodiment of the current invention, the protein markers are fused to the C-terminal end of the adenovirus fiber protein. In a further embodiment, the protein marker fused to the C-terminal end of the fiber protein gene contains six C-terminal histidine residues. In the preferred embodiment of the current invention, the protein marker is 6×His, consisting of the peptide sequence (RGSHHHHHH) (SEQ ID NO:9) fused to the end of the fiber protein gene by the linker peptide (PSASASASAP) (SEQ ID NO:8).

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 6 shows a specific interaction between the C-terminal His tag of the fiber protein of a modified virus and a n artificial His tag receptor permits propagation of Ad in U118MG cells. U118MG or U118MG-HissFv.rec cells were infected with either an adenovirus containing a wild-type fiber protein (Ad300wt) or with Ad5Fc6HIS. Four days post-infection, the cells were harvested and subjected to four rounds of freezing and thawing to release virus prior to reinfection of either U118MG or U118MG-HissFv.rec cells. Twenty-four hours later, immunohistochemistry was performed using rabbit anti-Ad5 antiserum as the primary antibody with a horseradish peroxidase conjugated goat anti-rabbit secondary antibody. DAB was employed as the chromogenic substrate.

DETAILED DESCRIPTION OF THE INVENTION

It is an object of the present invention to develop a system by which adenovirus vectors with native tropism ablated can still be propagated in a host cell line. This was accomplished by designing a novel tag on the adenovirus vector which can be recognized by a novel receptor on the cell surface of the host cell.

Figure 1A:
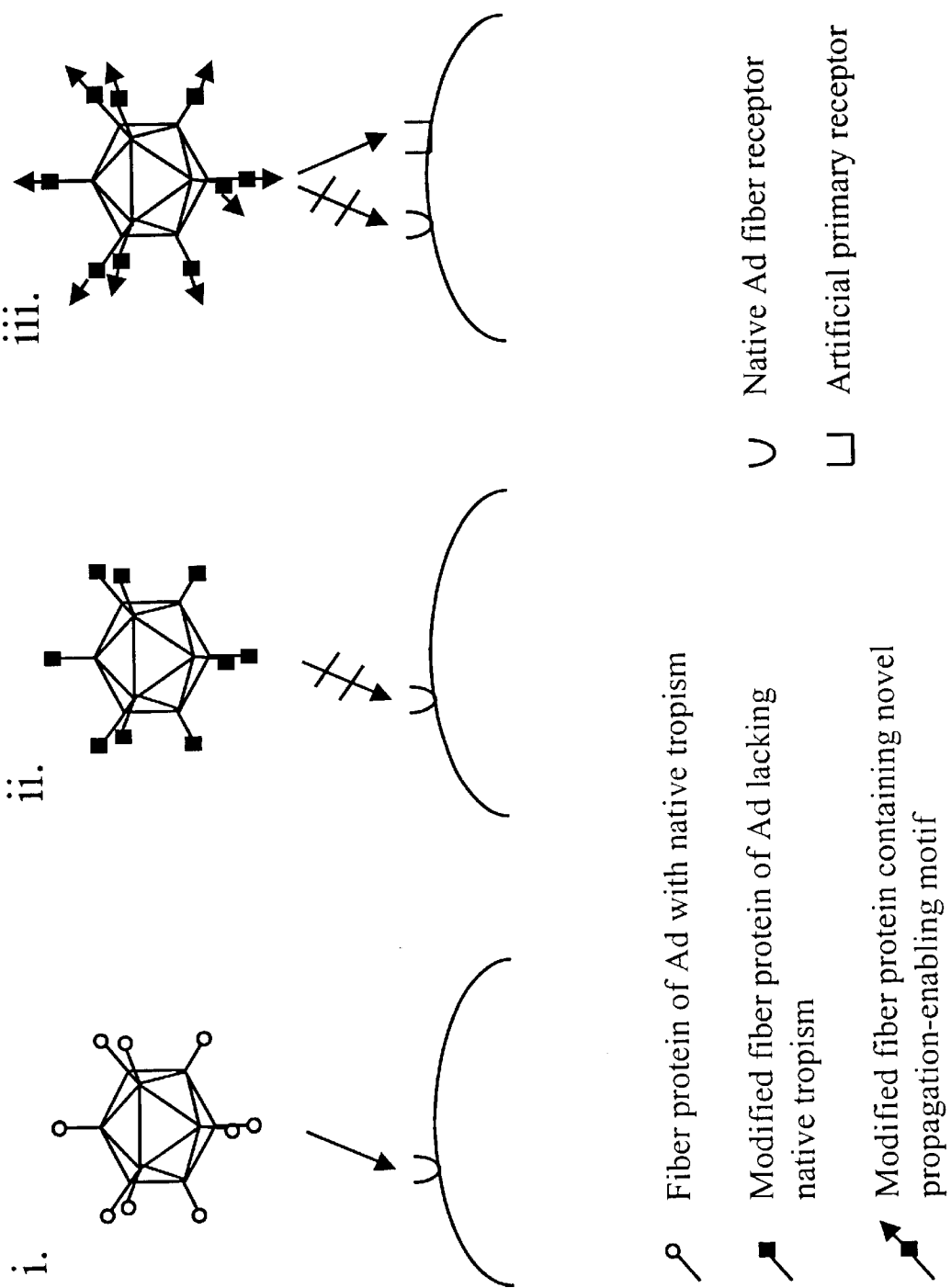
FIG. 1A shows the rationale used for the development of an artificial receptor to provide a fiber-receptor independent pathway of cellular entry for adenovirus vectors lacking native tropism. The first step in adenovirus infection is accomplished by the high affinity binding of the knob domain of the fiber to the primary cellular receptor. Elimination of the cell-binding domain ablates recognition of the native fiber receptor. A novel cell-binding mechanism is created by incorporating a universal propagation-enabling motif into the fiber protein to mediate attachment to a cognate artificial cellular receptor.
Figure 1B:
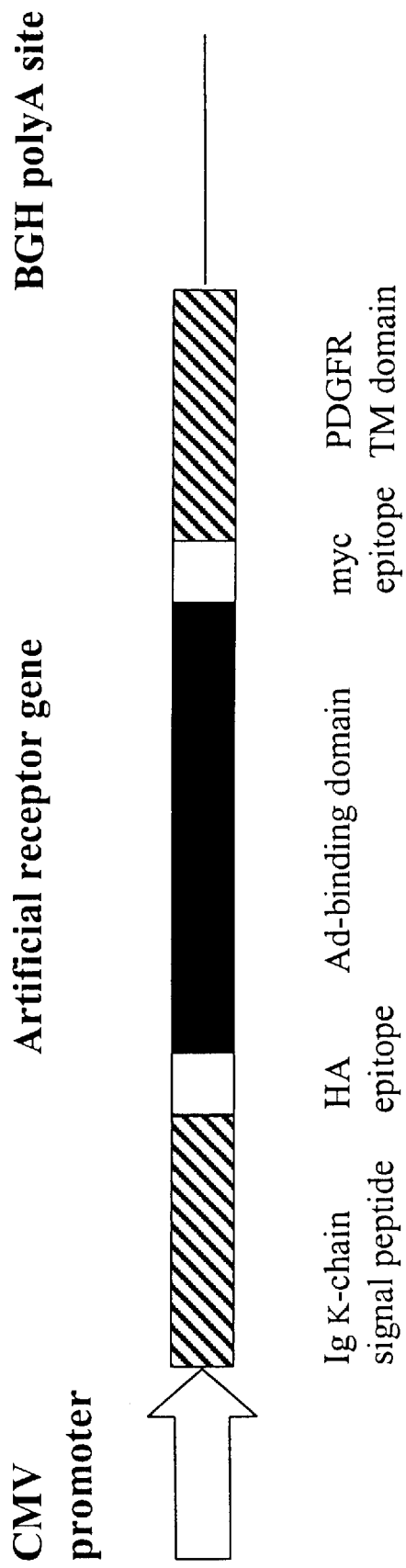
FIG. 1B shows a schematic diagram of the expression cassettes used for expression of the surface-displayed artificial receptors. The Ig K-chain leader sequence directs the receptor to the cell surface and the PDGFR transmembrane domain anchors the receptor in the plasma membrane. The HA epitope permits detection of the expressed protein by immunohistochemistry
Figure 2:
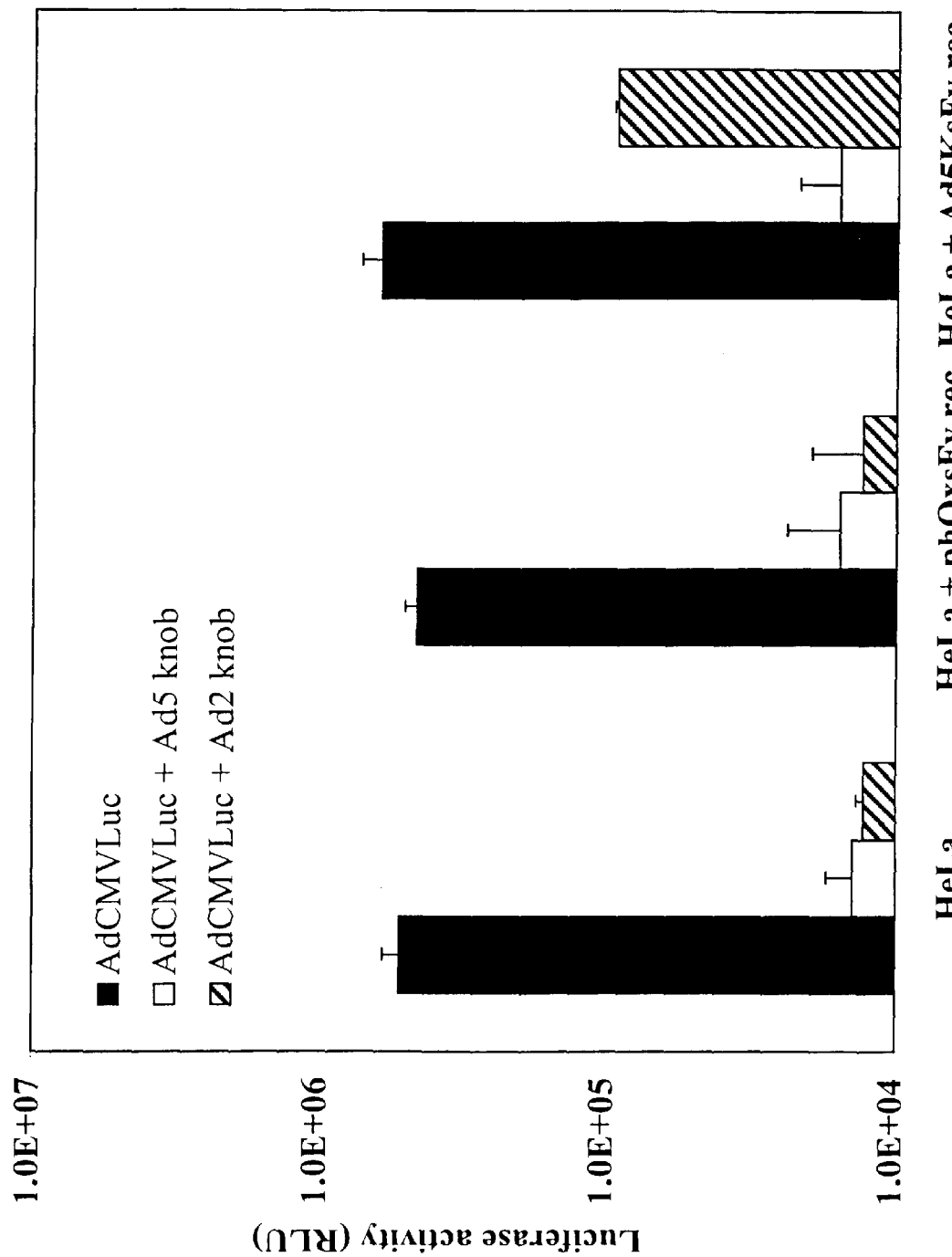
FIG. 2 shows that Ad5KsFv.rec functions as an artificial receptor to mediate fiber receptor-independent Ad5 infection of transfected HeLa cells. HeLa cells were mock-transfected or transfected with pAd5KsFv.rec or pHook, which expresses an irrelevant receptor, designated phOxsFv.rec. Forty-eight hours post-transfection, the cells were preincubated for 10 minutes at room temperature with PBS alone or with Ad2 or Ad5 knob at a concentration of 50 µg/ml in PBS. AdCMVLuc diluted in DMEM/F12+4% FCS was then added at an moi of 100 pfu per cell and the cells were incubated for 30 minutes at room temperature. The unbound virus was aspirated, the cells were washed, and then incubated with DMEM/F12+2% FCS for 1 hour at 37° C. and DMEM/F12+10% FCS for a further 24 hours. The cells were lysed and assayed for luciferase activity, which is expressed as relative light units per mg of cellular protein. Results are the mean of triplicate experiments.

As a first step towards the generation of cell lines expressing novel primary receptors that can be recognized by adenovirus vectors that fail to bind the fiber receptor, two distinct artificial primary cellular receptors for Ad5 were generated. Based on the concept that the native primary adenovirus cellular receptors function as high affinity docking sites for the fiber knob (28) with subsequent viral internalization mediated by αv integrins (12), an artificial primary receptor need merely serve to bind the virus to the cell surface. With this in mind, artificial receptors were engineered, each consisting of an extracellular domain with binding specificity for the Ad5 knob (FIGS. 1A and 1B).

The extracellular domain of one of the synthetic receptors was derived from a single-chain antibody (sFv) with specificity for Ad5 knob, while the second receptor consists of an icosapeptide which was identified from a phage display library by biopanning against Ad5 knob. Expression of either of these artificial receptors in fiber receptor-negative cells conferred susceptibility to Ad5 infection.

Having shown the feasibility of engineering novel primary receptors for Ad5, an Ad5 vector was then genetically modified by incorporating six histidine (His) residues at the C-terminal of the fiber to serve as a motif specifically to mediate propagation of the vector. This vector could be amplified in fiber receptor-negative cells engineered to express an artificial surface receptor comprising an anti-His tag sFv. This novel fiber receptor-independent system for the propagation of adenovirus viruses is being used for the generation of vectors lacking native tropism.

The present invention is directed to a method for the propagation of adenovirus in a host cell by means of an artificial, recombinant receptor expressed on the host cell. The receptor recognizes a surface protein on the virion to allow the adenovirus to first associate with the cell and then infect the cell. The artificial receptor allows for propagation of the adenovirus independent of the ubiquitous adenovirus fiber protein receptor.

The artificial receptor can be specific for a recombinant protein marker expressed on the surface of the adenovirus. One way this is accomplished is by adding the recombinant protein to the C-terminal end of the adenovirus fiber protein. In one example, the protein tag added to the fiber protein contained six C-terminal histidine residues, and the artificial receptor contained an sFv from an anti-His tag monoclonal antibody.

The present invention is also directed to the construction of a recombinant, artificial receptor to recognize the adenovirus vector. The receptor includes a signal peptide to direct the receptor to the cellular secretory pathway, a transmembrane domain for anchoring the receptor in the plasma membrane, and a protein binding domain specific for the protein marker the receptor is designed to recognize. In the examples cited here, the artificial receptor is constructed with a signal peptide from the Ig-K leader sequence, and a transmembrane domain from the Platelet Derived Growth Factor Receptor (PDGFR). The artificial also includes HA and Myc epitopes for immunological detection of the receptor. In one example, the protein binding domain of the artificial receptor was an sFv derived from an anti-His tag monoclonal antibody.

The present invention is also directed to the construction of a recombinant adenovirus expressing an novel protein marker for recognition by an artificial receptor. In the particular examples cited herein, the novel protein tag was added to the C-terminal end of the adenovirus fiber protein. The recombinant adenovirus may also include therapeutic genes, transgenes for genomic modification, or marker genes for adenovirus detection.

In the example most useful for the propagation of adenovirus with native tropism ablated, the protein marker contained six C-terminal histidine residues. Specifically, the C-terminal peptide was the sequence (RGSHHHHHH) (SEQ ID NO:9) fused to the end of the fiber protein genes by the linker peptide (PSASASASAP) (SEQ ID NO:8). This peptide is not recognized, by any known native markers, preventing inappropriate propagation of the adenovirus in nontarget cells. Furthermore, the C-terminal placement allows the rest of the fiber protein to be modified to add novel tropism and delete native tropism. In addition, the particular linker used does not interfere with trimerization of the fiber protein.

The following examples are given for the purpose of illustrating various embodiments of the invention and are not meant to limit the present invention in any fashion.

EXAMPLE 1

Construction of an Artificial Receptor with an sFv Derived From an Anti-Ad5 Knob Monoclonal Antibody The virus-binding domain of one of the novel receptors consisted of an sFv derived from a monoclonal antibody (mAb), designated 1D6.14 (13). This mAb is specifically directed against the trimeric Ad5 knob but fails to recognize the knob domain of Ad2, another human group C adenovirus.

The sFv was generated from the 1D6.14 hybridoma using a recombinant phage antibody system (Pharmacia Biotech, Pistcataway, N.J.). Briefly, mRNA was extracted from the hybridoma and reverse transcribed to generate cDNA. The variable heavy ($V_H$) and variable light ($V_L$) chains were amplified from the cDNA by PCR using mouse variable region primers. The $V_H$ and $V_L$ DNA fragments were joined by overlap extension PCR using a $(Gly_4Ser)_3$ linker to generate a 750-bp sFv construct with flanking Sfi I and Not I restriction sites which was cloned into the Sfi I/Not I sites of the phage display vector pCANTAB5E. Positive clones were identified by their ability to bind specifically to the trimeric Ad5 knob in an ELISA.

The sFv gene was amplified using PCR to add an Nco I site at the 5' end of the $V_H$ sequence and then subcloned into the Nco I/Not I sites of the pOPE51 prokaryotic expression vector (29). The anti-Ad5 knob sFv was expressed from this vector in *E. coli* TG1, purified from periplasmic inclusion bodies and renatured as described (29). The capacity of the refolded sFv to bind specifically to trimeric Ad5 knob was determined in an ELISA in which it was demonstrated to retain the ability of the parental 1D6.14 mAb to bind trimeric Ad5 knob (data not shown).

The gene encoding the anti-Ad5 knob sFv was amplified from pOPE51 by PCR using the primer pair 5'-GCT TGG CCC AGC CGG CCA TGG CCG-3' (SEQ ID NO:1) and 5'-GGC TGT CGA CTT TCA GCT CCA GCT TGG T-3' (SEQ ID NO:2). The PCR product was digested with Sfi I and Sal I and cloned into the corresponding sites in pDisplay (Invitrogen, Carlsbad, Calif.), producing pAd5KsFv.rec. The DNA fragment encoding the sFv receptor protein was fused in-frame at the 5' end to the DNA encoding the murine Ig K-chain leader sequence which directs the protein to the secretory pathway and the 3' end to the DNA encoding the transmembrane domain of platelet-derived growth factor receptor (PDGFR), which anchors the protein to the plasma membrane. In addition, the hemagglutinin A (HA) epitope was incorporated to permit detection of the cell surface receptors by immunological methods.

EXAMPLE 2

Figure 3A:
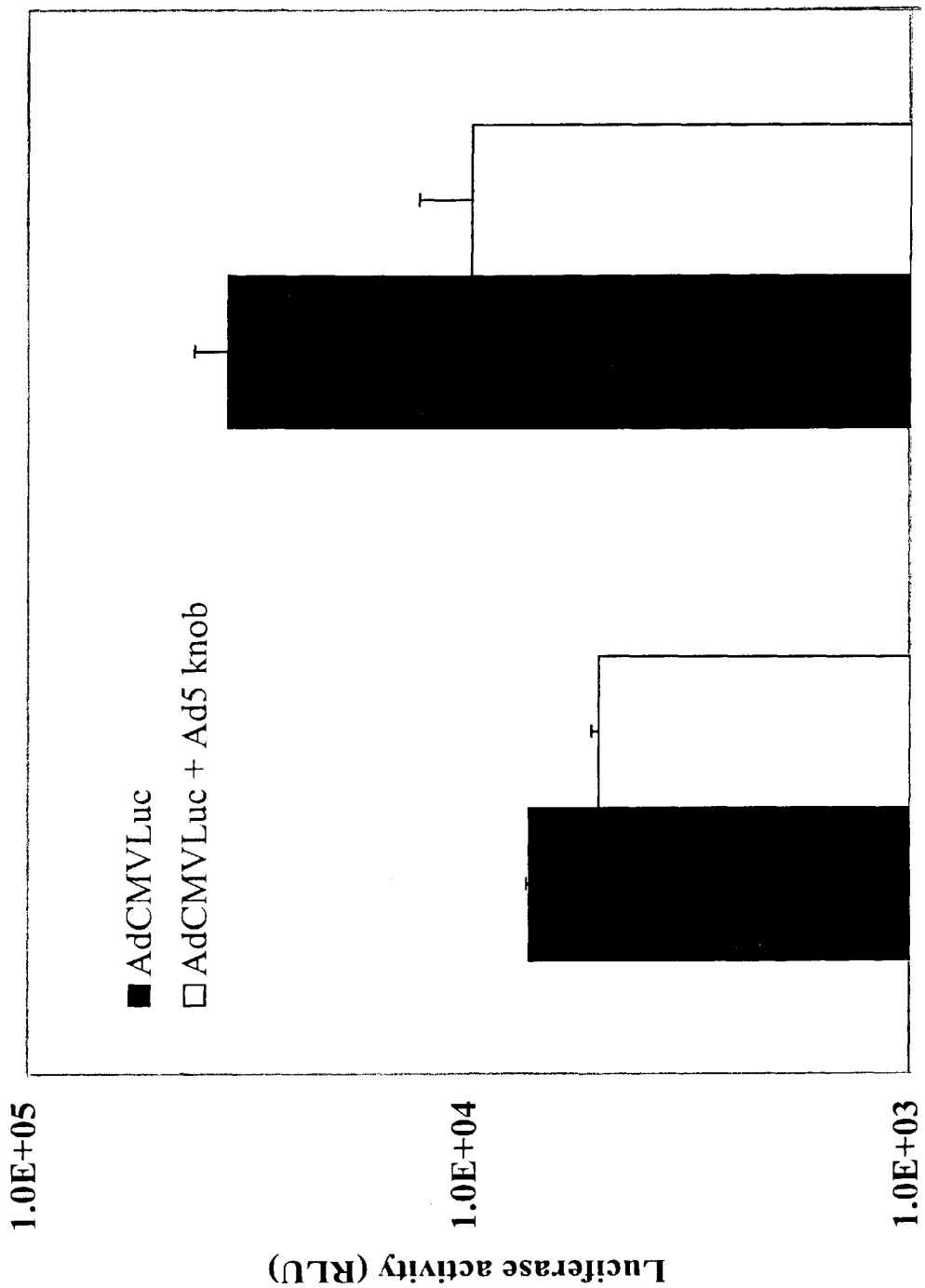
FIG. 3A shows parental U118MG cells, or stably transfected U118MG-phOxsFv.rec and U118MG-Ad5KsFv.rec cells which were preincubated with PBS or 50 µg/ml Ad5 knob prior to infection with AdCMVLuc. Results are the mean of triplicate experiments. Parental U118MG cells (FIG. 3B), or stably transfected U118MG-phOxsFv.rec (FIG. 3C) and U118MG-Ad5KsFv.rec (FIG. 3D) cells were exposed to AdCMVLacZ for 30 minutes at room temperature. The unbound virus was aspirated, the cells were washed, incubated with DMEM/F12+2% FCS for 1 hour at 37° C. and DMEM/F12+10% FCS for a further 24 hours. Expression of β-galactosidase was detected by staining with X-gal. Representative results are shown.

Construction of an Artificial Receptor With an Extracellular Virus-binding Domain Derived From an Icosavelitide The extracellular virus-binding domain of the second artificial receptor was an icosapeptide {designated MH20: RAIVGFRVQWLRYFVNGSR (SEQ ID NO:3)} identified by biopanning a phage display library with Ad5 knob (8). A pair of oligonucleotides encoding the MH20 icosapeptide {5'-TCG AAG AGG GCT ATA GTT GGG TTT AGG GTG CAA TGG CTT AGG CGG TAT TTT GTG AAT GGG TCG AGG A-3' (SEQ ID NO:4) and 5'-TCG ATC CTC GAC CCA TTC ACA AAA TAC CGC CTA AGC CAT TGC ACC CTA AAC CCA ACT ATA GCC CTC T-3' (SEQ ID NO:5)} was annealed. and ligated into the Sal I site of pDisplay, producing pMH20.rec. The cloning strategy was designed so that the insert was ligated in frame with the Ig K-chain leader sequence, HA epitope and PDGFR transmembrane domain.

EXAMPLE 3

Detection of the Artificial Receptors on the Cell Sulrface of Transfected HeLa Cells To confirm that the synthetic receptor proteins could be displayed on the cell surface, HeLa cells were transfected with each of the resultant plasmids (designated pAd5KsFv.rec and pMH20.rec) using AdpL. Twenty-four hours post-transfection, surface staining of 30% of cells was revealed by immunohistochemical analysis for hemagglutinin A (HA) epitope, indicating that the putative artificial receptors were correctly expressed (data not shown).

EXAMPLE 4

Ad5KsFv.rec Functions as an Artificial Receptor to Mediate Fiber Receptor-independent Ad5 Infection of Transfected HeLa Cells The ability of the Ad5KsFv.rec molecule to serve as a cellular receptor for Ad5 was then investigated. To this end, HeLa cells were employed, which are readily infected by Ad5 due to the abundant expression of fiber receptors which mediate virus binding and αv integrins which mediate virus internalization. HeLa cells were transfected with either pAd5KsFv.rec or with a control plasmid (pHook; Invitrogen) which has an identical design but expresses an irrelevant cell surface sFv against the phOx hapten. Forty-eight hours post-transfection, the HeLa cells were preincubated with recombinant Ad5 or Ad2 knob prior to infection with AdCMVLuc (30), an E1-deleted Ad5 vector which expresses firefly luciferase from the cytomegalovirus (CMV) promoter.

The recombinant Ad2 and Ad5 (35) were isolated from *E. coli*, where they had been expressed with N-terminal 6×His tags using the pQE30 expression vector and purified on Ni-NTA agarose (Qiagen). Both Ad5 and Ad2 knob proteins can block the binding of Ad5 viruses to the native primary Ad fiber receptors (9,10), whereas only the Ad5 knob is able to bind the artificial receptor, Ad5KsFv.rec.

After infection with AdCMVLuc, the cells were incubated for 24 hours and the luciferase activity was then determined. As shown in FIG. 2, expression of luciferase in both the mock-transfected HeLa cells, and the cells which expressed the irrelevant sFv, could b e reduced more than 95% by blocking with either the Ad5 or Ad2 knobs, indicating that viral infection of these cells was mediated by the native fiber receptors. Infection of the HeLa cells expressing Ad5KsFv.rec could also be blocked more than 95% by Ad5 knob. However, AdCMVLuc was able to infect HeLa-Ad5KsFv.rec cells despite preincubation with the Ad2 knob, which binds the native fiber receptor but not the anti-Ad5 sFv. This result indicates that Ad5KsFv.rec functions as an artificial receptor to mediate fiber receptor-independent Ad5 infection of transfected HeLa cells.

EXAMPLE 5

Ad5KsFv.rec Serves as an Artificial Receptor to Mediate Ad5 Infection of Fiber Receptor-negative Cells Whether this artificial receptor, Ad5KsFv.rec, could mediate Ad5 infection of fiber receptor-negative cells was then investigated. Murine Swiss 3T3-derived NR6 fibroblasts (32) and U118MG human glioma cells, which are refractory to adenovirus infection due to a paucity of fiber receptors, although they do express the αv integrins necessary for virus internalization (4), were transfected with pAd5KsFv.rec or the control plasmid pHook. Individual single cell clones were isolated, expanded by selection in the presence of G418, and tested for their susceptibility to adenovirus infection.

Nonpermissive NR6 and U118MG cells transfected with pAd5KsFv.rec became susceptible to infection by AdCMV- Luc (FIG. 3A and data not shown). In addition, adenovirus-mediated luciferase gene transfer to U118MG-Ad5KsFv.rec and NR6-Ad5KsFv.rec cells was inhibited by Ad5 knob. This indicates that binding of Ad5 to the artificial receptor Ad5KsFv.rec mediates infection of U118MG cells.

Figure 3B:
FIG. 3 shows that Ad5KsFv.rec functions as an artificial receptor to mediate Ad5 infection of nonpermissive U118MG cells. U118MG human glioma cells were transfected with pAd5KsFv.rec or the control plasmid pHook and individual single cell clones were isolated and expanded by selection in the presence of 400 µg/ml G418.
Figure 3C:
Figure 3D:
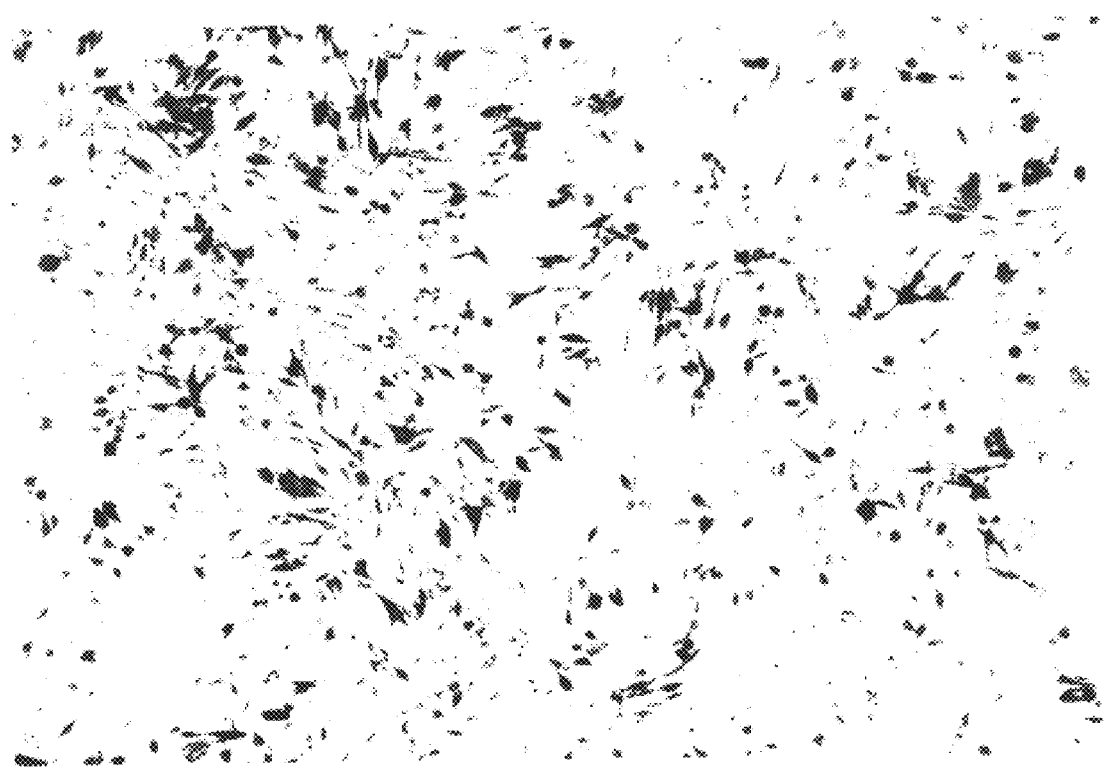

This finding was confirmed using AdCMVLacZ (33) an E1-deleted Ad5 vector which expresses *E. coli* β-galactosidase from the CMV promoter. Stable clones of U118MG cells and NR6 transfected with pAd5KsFv.rec, but not with the control plasmid, could be infected by AdCMVLacZ, as demonstrated by staining with X-gal (FIG. 3B–3D). Thus, Ad8KsFv.rec serves as an artificial receptor to mediate Ad5 infection of fiber receptor-negative cells.

EXAMPLE 6

Figure 4:
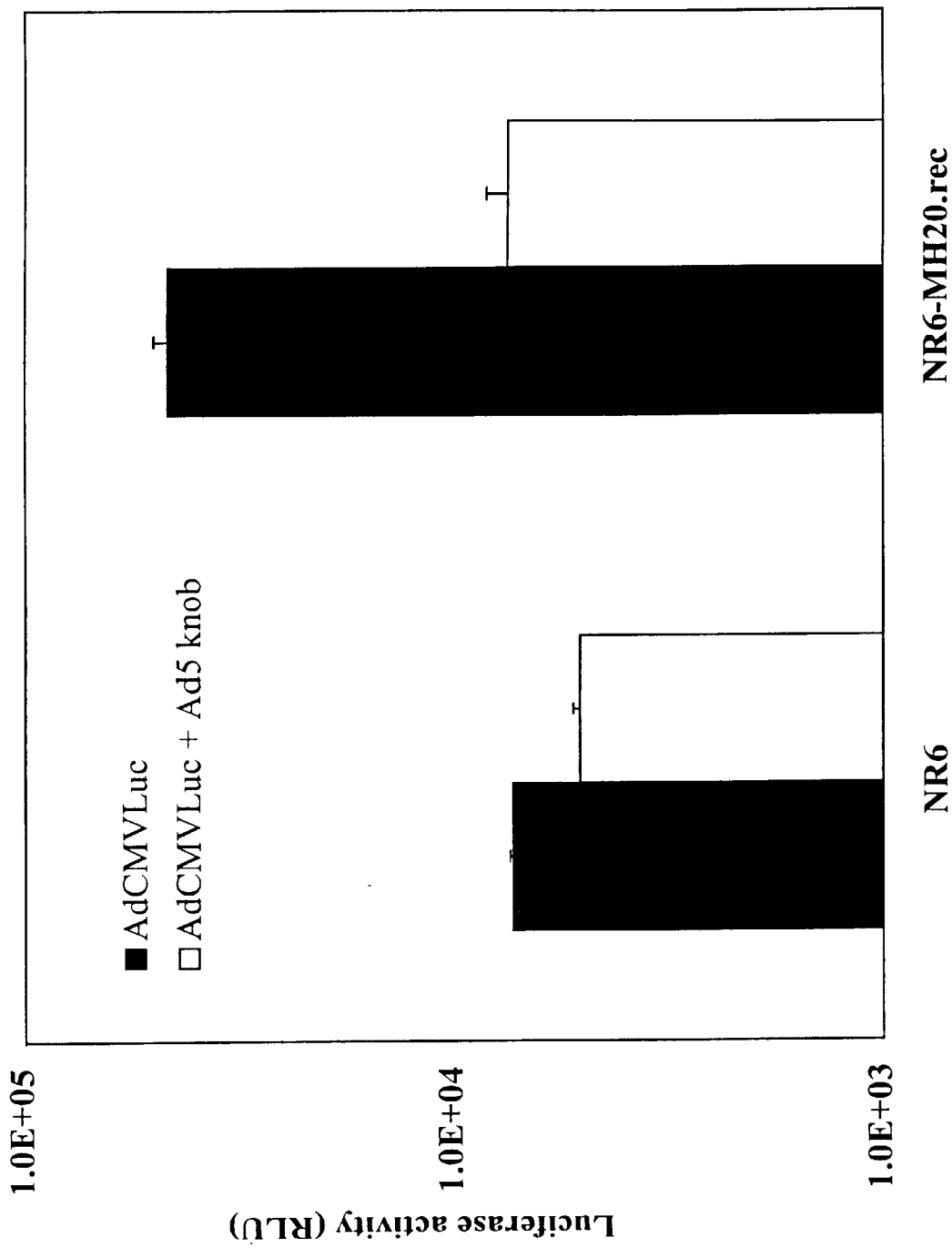
FIG. 4 shows that MH20.rec functions as an artificial receptor to mediate Ad5 infection of nonpermissive NR6 cells. NR6 murine fibroblasts were transfected with pMH20.rec and individual single-cell clones were isolated and expanded by selection in the presence of 1 mg/ml G418. Parental NR6 cells or stably transfected NR6-MH20.rec cells ($1.4 \times 10^5$) were preincubated with PBS or 50 µg/ml Ad5 knob prior to infection with AdCMVLuc at an moi of 100 as described for FIG. 2. Results are the mean of triplicate experiments.

MH20.rec Serves as an Artificial Receptor to Mediate Ad5 Infection of Fiber Recptor-negative Cells Having confirmed the functional utility of one of the novel artificial receptors for Ad5, the second synthetic receptor, MH20.rec, in which the extracellular domain consists of an icosapeptide with specificity for the Ad5 fiber knob was evaluated. Nonpermissive NR6 and U118MG cells were shown to become susceptible to Ad5-mediated gene transfer following surface expression of MH20.rec (FIG. 4 and data not shown).

It is possible to incorporate short peptide sequences into adenovirus capsid proteins where they can mediate virus-cell interactions by serving as receptor-binding ligands (3,23,24). The present invention shows that a peptide displayed on the cell surface can also mediate an interaction between the cell and the virus. Thus, two independently derived and conceptually distinct molecules, an sFv and an icosapeptide, can function as artificial receptors for Ad5 when expressed on the cell surface. Each of these receptor molecules possesses the ability to bind the knob domain of the Ad5 fiber, a feature they share with the native primary receptor. In addition, just as the primary adenovirus fiber receptor CAR serves as a high affinity docking site for the virus (28), the artificial receptors were designed simply to anchor the virus to the cell surface whereupon internalization would be mediated by αv integrins

EXAMPLE 7

Design Rationale for the Genetic Modification of Both the Virion and the Cell to Create a Novel Pathway of Cellular Entry The rationale for this study was to develop an artificial receptor which could provide a fiber receptor-independent pathway of cellular entry for Ad5 vectors lacking native tropism. It is advantageous to generate an artificial receptor that can be exploited to propagate any tropism-modified adenovirus vector, regardless of the target cell type. Such a universal artificial receptor avoids the necessity of engineering a specific receptor for each individual targeted adenovirus vector which, while theoretically possible, would prove extremely labor-intensive and time-consuming. Therefore, a completely novel cell-binding mechanism was created by genetically modifying both the virion and the cell (FIG. 1A).

The present invention demonstrates the incorporation into the adenovirus fiber knob of a peptide sequence for which there is no known natural cellular receptor and that therefore serves solely to recognize an artificial receptor expressed on the surface of cells in which the modified adenovirus vector is propagated. In considering exactly where to incorporate the universal propagation-enabling motif within the knob, three important criteria were met. First, it should not interfere with the ability of the fiber to trimerize. Second, the position of the propagation-enabling motif should be compatible with the strategy to retarget the adenovirus vector by the incorporation of peptide ligands into the so-called HI loop of the knob (3,25). Third, it should not preclude subsequent mutagenesis of the knob to ablate the native fiber receptor-binding site, the precise location of which is currently unknown. With these considerations in mind, a universal propagation-enabling motif consisting of six histidine (His) residues engineered at the C-terminal of the fiber was employed, which has previously been shown to be a n appropriate site for the incorporation of targeting motifs with specificity for cellular receptors (22–24). The cognate artificial receptor was designed to be a surface-displayed sFv with specificity for a C-terminal His tag (34).

EXAMPLE 8

Construction of an Ad5 Adenovirus Vector Displaying a Fiber Protein With a C-terminal His Tag The C-terminal of the fiber protein of an Ad5 vector was genetically modified by the addition of a short peptide linker followed by six His residues. In addition, the E1 region of the vector was substituted by a luciferase expression cassette.

Ad5lucFc6HIS, which possesses His tag additions to the C-terminal of the fiber protein was constructed in the following manner. To design a gene encoding the Ad5 fiber protein with a C-terminal 6×His tag, fiber-6HIS, a duplex made of two oligonucleotides 5'-CCA TCA GCC TCC GCA TCT GCT TCC GCC CCT GGA TCG AGA GGA TCG CAT CAC CAT CAC CAT CAC TAA TAA ACC CGA TCC TAA-3' (SEQ ID NO:6) and 5'-TTA GGA TCG GGT TTA TTA GTG ATG GTG ATG GTG ATG CGA TCC TCT CGA TCC AGG GGC GGA AGC AGA TGC GGA GGC TGA TGG-3' (SEQ ID NO:7) was cloned into EcoICRI-cleaved pBS.F5.UTR37. This resulted in the addition of a short peptide linker (PSASASASAP) (SEQ ID NO:8) and a six-His containing peptide (RGSHHHHHH) (SEQ ID NO:9) to the C-terminal of the wild-type fiber protein. The modified portion of the fiber gene was isolated as a BstX I-Mfe I fragment from the resultant plasmid, pBS.F5.RGS6HSL, and then cloned into the BstX I-Mfe I-cleaved fiber shuttle vector, pNEB.PK3.637 to replace the corresponding segment of the wild type fiber gene. This newly designed plasmid, pNEB.PK.RGS6HSL, was used for homologous DNA recombination in *E. coli* with the previously described pVK5025 in order to generate a recombinant adenovirus genome containing the fiber-6HIS gene. The resultant plasmid was designated pVK100. Finally, the E1 region of the adenovirus genome contained in pVK100 was replaced with the firefly luciferase expression cassette excised from pACCMV.LucDPC as described by Dmitriev et al. (3), thereby generating pVK712.

Transfection of 293 cells with Pac I-digested pVK712 resulted in the rescue of Ad5lucFc6HIS (25,35). The identity of the virus was confirmed by partial sequencing of DNA isolated from purified virions as well as by Western blot analysis of viral proteins performed with anti-fiber mAb 4D222 and the anti-six-His mAb RGSHIS (Qiagen, Valencia, Calif.). The resultant virus retained the ability to recognize the fiber receptor (data not shown), and was therefore propagated on the E1-complementing 293 cell line. The accessibility of the His tag in the intact viral particle was verified by the ability of the virion to bind specifically to nickel-nitrilotriacetic acid (Ni-NTA) agarose (data not shown).

EXAMPLE 9

Construction of an Artificial Receptor With an sFv Derived From an Anti-His Tag Monoclonal Antibody The next step was to construct an artificial receptor capable of interacting with the modified His tag fiber protein. The Sfi I fragment encoding the anti-His tag sFv was excised from pAK100His233, from Andreas Pluckthun (University of Zurich, Zurich, Switzerland). In order to facilitate incorporation of this Sfi I fragment, pDisplay was modified by digestion with Sal I and insertion of a linker formed by the oligonucleotide pair 5'-TCG AGG CCT CGG GGG CCA-3' (SEQ ID NO:10) and 5'-TCG ATG GCC CCC GAG GCC-3' (SEQ ID NO:11), which destroyed the Sal I site and introduced a second Sfi I site (underlined). The cloning strategies were designed so that the insert was ligated in frame with the Ig K-chain leader sequence, HA epitope and PDGFR transmembrane domain.

U118MG human glioma cells were transfected with the resultant plasmid, pHissFv.rec. Individual single-cell clones were isolated and expanded by selection in the presence of G418. One of these clones, which exhibited surface expression of the HissFv.rec molecule as verified by immunohistochemistry (data not shown), was used in the subsequent experiments.

EXAMPLE 10

Figure 5:
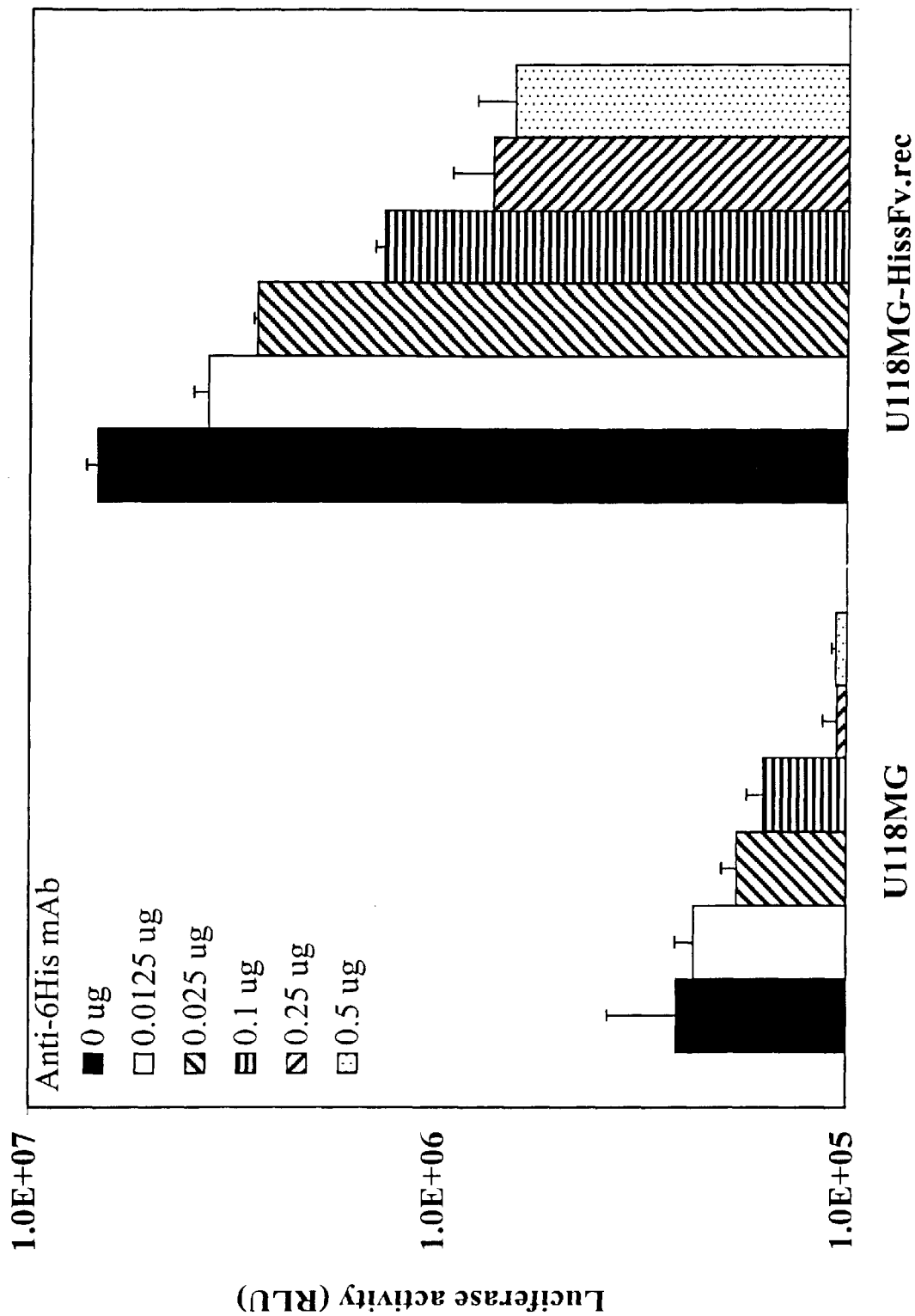
FIG. 5 shows that a specific interaction between the C-terminal His tag of the fiber protein of a modified virus and a n artificial His tag receptor mediates infection of nonpermissive U118MG cells. U118MG human glioma cells were transfected with pHissFv.rec and individual single-cell clones were isolated and expanded by selection in the presence of 400 µg/ml G418. Varying dilutions of an anti-His mAb were incubated with Ad5lucFc6HIS at room temperature in a total volume of 20 µl HBS. After 30 minutes, the volume was increased to 1 ml with DMEM/F-12+2% FCS and 250 µl of the complexes were added to 24-well plates containing $1.4 \times 10^5$ U118MG or U118MG-HissFv.rec cells previously rinsed with PBS. The experiment was then conducted as described for FIG. 2. Results are the mean of triplicate experiments.
Figure 6A:
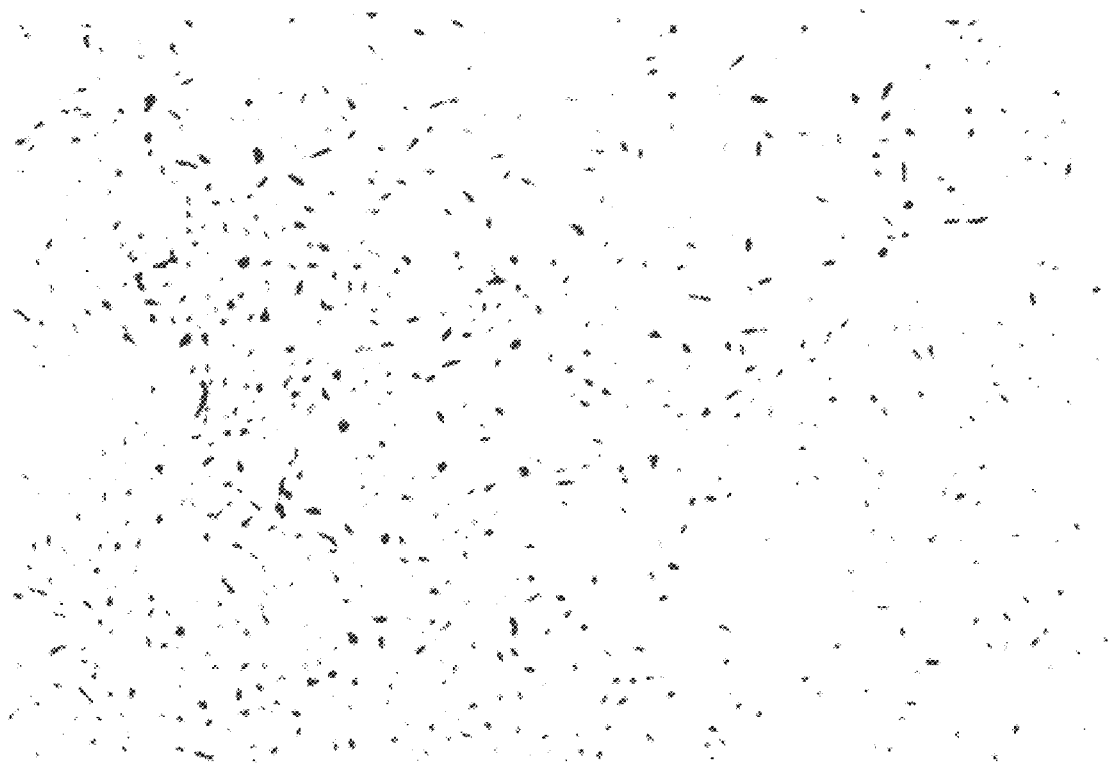
(FIG. 6A). Cell: U118MG; virus: Ad300wt.
Figure 6B:
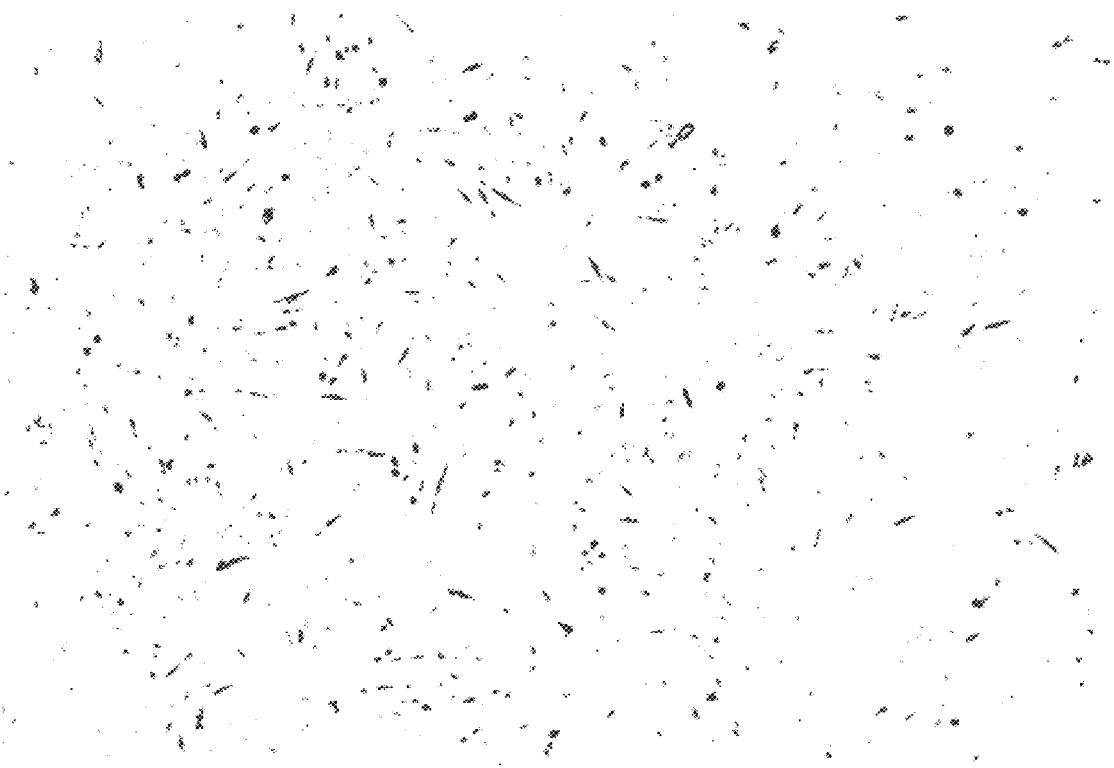
(FIG. 6B). Cell: U118MG-HissFv.rec; virus: Ad300wt.
Figure 6C:
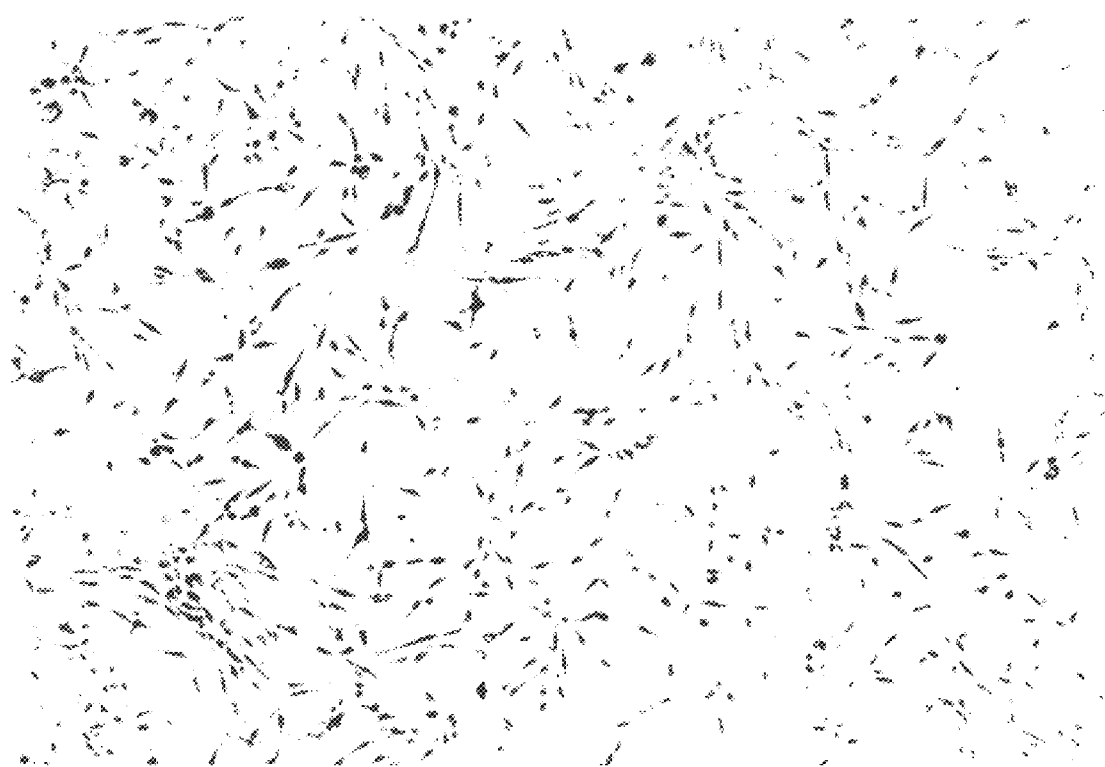
(FIG. 6C). Cell: U118MG; virus: Ad5Fc6HIS.
Figure 6D:
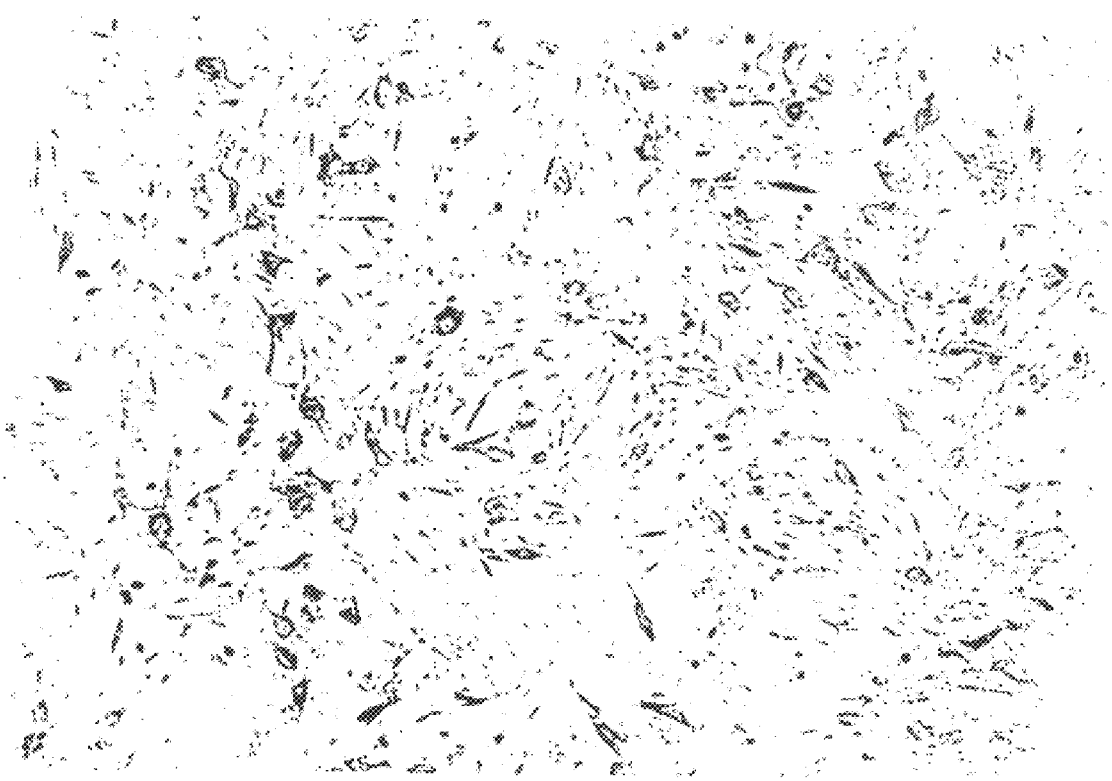
(FIG. 6D). Cell: U118MG-HissFv.rec; virus: Ad5Fc6HIS.

The Surface-displayed HissFv.rec Molecule Acts as an Artificial Primary Receptor for Ad5lucFc6HIS While the parental U118MG cells were refractory to Ad5lucFc6HIS, this virus was able to infect the stably transfected U118MG-HissFv.rec cells (FIG. 5). Preincubation of Ad5lucFc6HIS with an anti-His mAb inhibited infection of the U1 18MG.HissFv.rec cells in a dose-dependent manner. These results demonstrate that the modified virus, Ad5lucFc6HIS, infected U118MG.HissFv.rec cells by means of a specific interaction between the C-terminal His tag of the fiber protein and the artificial His tag receptor.

EXAMPLE 11

Propagation of the Modified His Tag Ad5 Vector in the Anti-His Tag sFv Cell Line This novel cell-binding mechanism provided by the His tag addition to the C-terminal of the Ad5 fiber and its cognate artificial cellular receptor can be exploited to permit propagation of the adenovirus vector. An analysis of the propagation of Ad5lucFc6HIS in E1-complementing cell lines such as 293 or 911 would have been confounded by the presence of fiber receptors. Hence it was necessary to use the Ad5 virus designated Ad5Fc6HIS, which possessed the His tag modification of the fiber protein but retained an intact E1 region and was therefore not dependent upon the provision of this region in trans to enable replication. This virus was constructed by the transfection of 293 cells with Pac I-digested pVK100 from Example 8 to result in the rescue of Ad5Fc6HIS (25,35). The identity of the virus was confirmed by partial sequencing of DNA isolated from purified virions as well as by Western blot analysis of viral proteins performed with anti-fiber mAb 4D222 and the anti-six-His mAb RGSHIS (Qiagen, Valencia, Calif.). Both parental U118MG cells and U118MG-HissFv.rec cells, which express the artificial His tag receptor, were infected with either Ad5Fc6HIS or a control wild-type Ad5 virus, Ad300 wt. Four days post-infection, a cytopathic effect could be observed in U118MG-HissFv.rec cells infected with Ad5Fc6HIS, but not in the control cells. At this time, the cells were harvested and after four rounds of freezing and thawing the cell lysates were used to reinfect either U118MG or U118MG-HissFv.rec cells. Twenty-four hours later, immunohistochemistry was performed with rabbit anti-Ad5 antiserum. As shown in FIG. 6, it was necessary both for the Ad5 fiber protein to contain the His tag and for the fiber receptor-negative cell line to express the His receptor in order for the virus to be propagated. This demonstrates that these two complementary components together constitute a novel system that permits the fiber receptor-independent propagation of Ad5 vectors.

This study paves the way for the construction of targeted Ad5 vectors possessing true specificity for a single cell type. The addition of a C-terminal His tag to the fiber protein of an Ad5 vector specifically mediates cellular entry via an artificial receptor. Hence, by retaining this propagation-enabling motif, for which there is no known natural cellular receptor, it should be possible to generate adenovirus vectors in which the ability to recognize the fiber receptor has been ablated and into which a new targeting specificity has been introduced.

Moreover, it should be possible to engineer the His tag into other sites in the viral capsid proteins chosen to be compatible with alternative targeting strategies. In this regard, the adenovirus hexon and penton base proteins have been shown to accommodate short peptide sequences (36, 37). This technology, comprising a genetically engineered adenovirus virion and a modified cell line, should therefore facilitate further advances in the design of adenovirus vectors for gene therapy.

The following references were cited herein:

1. Zabner, J., Freimuth, P., Puga, A., A., F. and Walsh, M. J. 1997. Lack of high affinity fiber receptor activity explains the reistance of ciliated airway epithelia to adenovirus infection. Journal of Clinical Investigation 100:1144–1149.
2. Pickles, R. J., McCarty, D., Matsui, H., Hart, P. J., Randell, S. H. and Boucher, R. C. 1998. Limited entr of adenovirus vectors into well-differentiated airway epithelium is responsible for inefficient gene transfer. Journal of Virology 72:6014–6023.
3. Dmitriev, I., Krasnykh, V., Miller, C. R., Wang, M., Kashentseva, E., Mikheeva, G., Belousova, N. and Curiel, D. T. 1998. An adenovirus vector with gentically modified fibers demonstrates expanded tropism via utilization of a coxsackievirus and adenovirus receptor-independent cell entry mechanism. Journal of Virology 72:9706–9713.
4. Miller, C. R., Buchsbaum, D. J., Reynolds, P. N., Douglas, J. T., Gillespie, G. Y., Mayo, M. S., Raben, D. and Curiel, D. T. 1998. Differential susceptibility of primary and established human glioma cells to adenovirus infection: Targeting via the epidermal growth factor receptor achieves fiber receptor-independent gene transfer. Cancer Research
5. Bergelson, J. M., Cunningham, J. A., Droguett, G., Kurt-Jones, E. A., Krithivas, A., Hong, J. S., Horwitz, M. S., Crowell, R. L. and Finberg, R. W. 1997. Isolation of a common receptor for coxsackie B viruses and adenoviruses 2 and 5. Science 275: 1320–1323.

6. Tomko, R. P., Xu, R. and Philipson, L. 1997. HCAR and MCAR: the human and mouse cellular receptors for subgroup C adenoviruses and group B coxsackieviruses. Proceedings of the National Academy of Sciences of the United States of America 94:3352–3356.
7. Bergelson, J. M., Krithivas, A., Celi, L., Droguett, G., Horwitz, M. S., Wickham, T., Crowell, R. L. and Finberg, R. W. 1998. The murine CAR homolog is a receptor for coxsackie B viruses and adenoviruses. Journal of Virology 71:415–419.
8. Hong, S. S., Karayan, L., Tournier, J., Curiel, D. T. and Boulanger, P. A. 1997. Adenovirus type 5 fiber knob binds to MHC class I alpha2 domain at the surface of human epithelial and B lymphoblastoid cells. EMBO Journal 16:2294–2306.
9. Henry, L. J., Xia, D., Wilke, M. E., Deisenhofer, J. and Gerard, R. D. 1994. Characterization of the knob domain of the adenovirus type 5 fiber protein expressed in *Escherichia coli*. Journal of Virology 68:5239–5246.
10. Louis, N., Fender, P., Barge, A., Kitts, P. and Chroboczek, J. 1994. Cell-binding domain of adenovirus serotype 2 fiber. Journal of Virology 68:4104–4106.
11. Bai, M., Harfe, B. and Freimuth, P. 1993. Mutations that alter an Arg-Gly-Asp (RGD) sequence in the adenovirus type 2 penton base protein abolish its cell-rounding activity and delay virus reproduction in flat cells. Journal of Virology 67:5198–5205.
12. Wickham, T. J., Mathias, P., Cheresh, D. A. and Nemerow, G. R. 1993. Integrins alpha v beta 3 and alpha v beta 5 promote adenovirus internalization but not virus attachment. Cell 73:309–319.
13. Douglas, J. T., Rogers, B. E., Rosenfeld, M. E., Michael, S. I., Feng, M. and Curiel, D. T. 1996. Targeted gene delivery by tropism-modified adenoviral vectors. Nature Biotechnology 14:1574–1578.
14. Wickham, T. J., Segal, D. M., Roelvink, P. W., Carrion, M. E., Lizonova, A., Lee, G. M. and Kosvedi, I. 1996. Targeted adenovirus gene transfer to endothelial and smooth muscle cells by using bispecific antibodies. Journal of Virology 70:683 1–6838.
15. Goldman, C. K., Rogers, B. E., Douglas, J. T., Sosnowski, B. A., Ying, W., Siegal, G. P., Baird, A., Campain, J. A. and Curiel, D. T. 1997. Targeted gene delivery to Kaposi's sarcoma cells via the fibroblast growth factor receptor. Cancer Research 57:1447–1451.
16. Rogers, B. E., Douglas, J. T., Ahlem, C., Buchsbaum, D. J., Frincke, J. and Curiel, D. T. 1997. Use of a novel cross-linking method to modify adenoviral tropism. Gene Therapy 4:1387–1392.
17. Rogers, B. E., Douglas, J. T., Sosnowski, B. A., Ying, W., Pierce, G., Buchsbaum, D. J., DellaManna, D., Baird, A. and Curiel, D. T. 1998. Enhanced in vivo gene delivery to human ovarian cancer xenografts utilizing a tropism-modified adenovirus vector. Tumor Targeting 3:25–31.
18. Watkins, S. J., Mesyanzhinov, V. V., Kurochkina, L. P. and Hawkins, R. E. 1997. The adenobody approach to viral targeting specific and enhanced adenoviral gene delivery. Gene Therapy 4:1004–1012.
19. Wickham, T. J., Lee, G. M., Titus, J. A., Sconocchia, G., Bakacs, T., Kovesdi, I. and Segal, D. M. 1997. Targeted adenovirus-mediated gene delivery to T cells via CD3. Journal of Virology 71:7663–7669.
20. Rancourt, C., Rogers, B. E., Sosnowski, B. A., Wang, M., Piche, A., Pierce, G. F., Alvarez, R. D., Siegal, G. P., Douglas, J. T. and Curiel, D. T. 1998. Basic fibroblast growth factor enhancement of adenovirus-mediated delivery of the herpes simplex virus thymidine kinase gene results in augmented therapeutic benefit in a murine model of ovarian cancer. Clinical Cancer Research 4:2455–2461.
21. Reynolds, P. N., Miller, C. R., Goldman, C. K., Doukas, J., Sosnowski, B. A., Rogers, B. E., Gomez-Navarro, J., Pierce, G. F., Curiel, D. T. and Douglas, J. T. 1998. Targeting adenoviral infection with basic fibroblast growth factor enhances gene delivery to vascular endothelial and smooth muscle cells. Tumor Targeting
22. Michael, S. I., Hong, J. S., Curiel, D. T. and Engler, J. A. 1995. Addition of a short peptide ligand to the adenovirus fiber protein. Gene Therapy 2:660–668.
23. Wickham, T. J., Roelvink, P. W., Brough, D. E. and Kovesdi, I. 1996. Adenovirus targeted to heparan-containing receptors increases its gene delivery efficiency to multiple cell types. Nature Biotechnology 14:1570–1573.
24. Wickham, T. J., Tzeng, E., Shears, L. L., Roelvink, P. W., Li, Y., Lee, G. M., Brough, D. E., Lizonova, A. and Kovesdi, I. 1997. Increased in vitro and in vivo gene transfer by adenovirus vectors containing chimeric fiber proteins. Journal of Virology 71:8221–8229.
25. Krasnykh, V. N., Dmitriev, I., Mikheeva, G., Miller, C. R., Belousova, N. and Curiel, D. T. 1998. Characterization of an adenoviral vector containing a heterologous peptide epitope in the HI-loop of the fiber knob. Journal of Virology 72:1844–1852.
26. Graham, F., Smiley, J., Russell, W. and Nairn, R. 1977. Characteristics of a human cell line transformed by DNA from human adenovirus type 5. Journal of General Virology 36:59–72.
27. Fallaux, F. J., Kranenburg, O., Cramer, S. J., Houweling, A., van Ormondt, H., Hoeben, R. C. and van der Eb, A. J. 1996. Characterization of 911: A new helper cell line for the titration and propagation of early region 1-deleted adenoviral vectors. Human Gene Therapy 7:215–222.
28. Leon, R. P., Hedlund, T., Meech, S. J., Li, S., Schaack, J., Hunger, S. P., Duke, R. C. and DeGregori, J. 1998. Adenoviral-mediated gene transfer in lymphocytes. Procedins of the National Academy of Sciences of the U.S.A. 95:13159–13164.
29. Kipriyanov, S. M., Dubel, S., Breitling, F., Kontermann, R. E. and Little, M. 1994. Recombinant single-chain Fv fragments carrying C-terminal cysteine residues: production of bivalent and biotinylated miniantibodies. Molec. Immunol. 31:1047–1058.
30. Herz, J. and Gerard, R. D. 1993. Adenovirus-mediated transfer of low density lipoprotein receptor gene acutely accelerates cholesterol clearance in normal mice. Proceedings of the National Academy of Sciences of the United States of America 90:2812–2816.
31. Krasnykh, V. N., Mikheeva, G. V., Douglas, J. T. and Curiel, D. T. 1996. Generation of recombinant adenovirus vectors with modified fibers for altering viral tropism. Journal of Virology 70:6839–6846
32. Chen, P., Gupta, K. and Wells, A. 1994. Cell movement elicited by the epidermal growth factor requires kinase and autophosphorylation but is separable from mitogenesis. Journal of Cell Biology 124:547–555.
33. Kolls, J., Peppel, K., Silva, M. and Beutler, B. 1994. Prolonged and effcetive blockade of tumor necrosis factor activity through adenovirus-mediated gene transfer. Proccedings of the National Academy of Sciences of the U.S.A. 91:215–219.
34. Lindner, et al., 1997. Specific detection of His-tagged proteins with recombinat anti-His tag scFv-phosphatase or scFv phage fusions. BioTechniques 22:140–149.

35. Chartier, C., Degryse, E., Gantzier, M., Dieterle, A., Pavirani, A. and Mehtali, M. 1996. Efficient generation of recombinant adenovirus vectors by homologous recombination in *Escherichia coli*. Journal of Virology 70:4805–4810.
36. Crompton, et al. 1994. Journal of General Virology 75:133–139.
37. Wickham, T. J., Carrion, M. E. and Kovesdi, I. 1995. Gene Therapy 2:750–756.

Any patents or publications mentioned in this specification are indicative of the levels of those skilled in the art to which the invention pertains. These patents and publications are incorporated by reference to the same extent as if each individual publication was individually indicated as incorporated by reference.

One skilled in the art will readily appreciate that the present invention is well adapted to carry out the objects and obtain the ends and advantages mentioned, as well as those inherent therein. The present examples along with the methods, procedures, treatments and molecules described herein are representative of preferred embodiments, are exemplary, and are not limitations on the scope of the invention. Changes therein and other uses will occur to those skilled in the art which are encompassed within the spirit of the invention as defined by the scope of the claims.

What is claimed is:

1. A method for the propagation of adenovirus in a host cell, comprising the steps of:

expressing a non-native recombinant receptor on the surface of a host cell, wherein said receptor comprises a sFv from an anti-His tag monoclonal antibody; and infecting said host cell with an adenovirus comprising a y histidine tag added to the C-terminal end of the adenovirus fiber protein, wherein said addition of histidine tag is not functionally linked to ablation of native virus tropism, and said adenovirus infects said host cell by interacting with said recombinant receptor so as to allow the propagation of said adenovirus within said host cell.

* * * * *

SEQUENCE LISTING

<160> NUMBER OF SEQ ID NOS: 11

<210> SEQ ID NO 1
<211> LENGTH: 24
<212> TYPE: DNA
<213> ORGANISM: artificial sequence
<220> FEATURE:
<221> NAME/KEY: primer
<223> OTHER INFORMATION: primer used to amplify gene encoding anti-Ad5
    sFv from pOPE51

<400> SEQUENCE: 1
gcttggccca gccggccatg gccg                                              24

<210> SEQ ID NO 2
<211> LENGTH: 28
<212> TYPE: DNA
<213> ORGANISM: artificial sequence
<220> FEATURE:
<221> NAME/KEY: primer
<223> OTHER INFORMATION: primer used to amplify gene encoding anti-Ad5
    sFv from pOPE51

<400> SEQUENCE: 2
ggctgtcgac tttcagctcc agcttggt                                          28

<210> SEQ ID NO 3
<211> LENGTH: 20
<212> TYPE: PRT
<213> ORGANISM: artificial sequence
<220> FEATURE:
<223> OTHER INFORMATION: amino acid sequence of the icosapeptide MH20;
    the extracellular virus-binding domain of the second artificial
    receptor

<400> SEQUENCE: 3

Arg Ala Ile Val Gly Phe Arg Val Gln Trp Leu Arg Arg Tyr Phe
                5                   10                  15

Val Asn Gly Ser Arg
            20

<210> SEQ ID NO 4
<211> LENGTH: 64
<212> TYPE: DNA
<213> ORGANISM: artificial sequence
<220> FEATURE:
<223> OTHER INFORMATION: oligonucleotide encoding the MH20 icosapeptide

<400> SEQUENCE: 4
aagagggcta tagttgggtt tagggtgcaa tggcttaggc ggtattttgt                  50

```
gaatgggtcg agga                                                   64

<210> SEQ ID NO 5
<211> LENGTH: 67
<212> TYPE: DNA
<213> ORGANISM: artificial sequence
<220> FEATURE:
<223> OTHER INFORMATION: oligonucleotide encoding the MH20 icosapeptide

<400> SEQUENCE: 5
tcgatcctcg acccattcac aaaatacgcg ctaagccatt gcaccctaaa            50
cccaactata gccctct                                                67

<210> SEQ ID NO 6
<211> LENGTH: 81
<212> TYPE: DNA
<213> ORGANISM: artificial sequence
<220> FEATURE:
<223> OTHER INFORMATION: oligonucleotide cloned into EcoICRI-cleaved
      pBS.F5.UTR37

<400> SEQUENCE: 6
ccatcagcct ccgcatctgc ttccgcccct ggatcgagag gatcgcatca            50
ccatcaccat cactaataaa cccgatccta a                                81

<210> SEQ ID NO 7
<211> LENGTH: 81
<212> TYPE: DNA
<213> ORGANISM: artificial sequence
<220> FEATURE:
<223> OTHER INFORMATION: oligonucleotide cloned into EcoICRI-cleaved
      pBS.F5.UTR37

<400> SEQUENCE: 7
ttaggatcgg gtttattagt gatggtgatg gtgatgcgat cctctcgatc            50 cagggggcgga agcagatgcg gaggctgatg g                               81

<210> SEQ ID NO 8
<211> LENGTH: 10
<212> TYPE: PRT
<213> ORGANISM: artificial sequence
<220> FEATURE:
<223> OTHER INFORMATION: short peptide linker used to fuse the six-His
      containing peptide to C-terminal of the wild-type
      fiber protein

<400> SEQUENCE: 8

Pro Ser Ala Ser Ala Ser Ala Ser Ala Pro
            5                   10

<210> SEQ ID NO 9
<211> LENGTH: 9
<212> TYPE: PRT
<213> ORGANISM: artificial sequence
<220> FEATURE:
<223> OTHER INFORMATION: six-His containing peptide added to C-terminal
      of the wild-type fiber protein

<400> SEQUENCE: 9

Arg Gly Ser His His His His His His
            5

<210> SEQ ID NO 10
<211> LENGTH: 18
<212> TYPE: DNA
```

```
<213> ORGANISM: artificial sequence
<220> FEATURE:
<223> OTHER INFORMATION: oligonucleotide linker used to introduce a
      Sfi I site into the Sfi I fragment encoding the anti-His tag sFv

<400> SEQUENCE: 10
tcgaggcctc gggggcca                                                 18

<210> SEQ ID NO 11
<211> LENGTH: 18
<212> TYPE: DNA
<213> ORGANISM: artificial sequence
<220> FEATURE:
<223> OTHER INFORMATION: oligonucleotide linker used to introduce a
      second Sfi I site into the Sfi I fragment encoding the anti-His
      tag sFv

<400> SEQUENCE: 11
tcgatggccc ccgagcgg                                                 18
```